(12) United States Patent  
Wynn

(10) Patent No.: US 8,651,702 B2
(45) Date of Patent: Feb. 18, 2014

(54) SELF-ALIGNING LIGHT SOURCE AND DETECTOR ASSEMBLY

(75) Inventor: William H. Wynn, Hillsborough, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 635 days.

(21) Appl. No.: 12/795,501

(22) Filed: Jun. 7, 2010

(65) Prior Publication Data

US 2011/0299289 A1    Dec. 8, 2011

(51) Int. Cl.
*F21V 23/04* (2006.01)

(52) U.S. Cl.
USPC ............................................. 362/276

(58) Field of Classification Search
USPC ................ 362/138, 139, 141–143, 276, 287
See application file for complete search history.

(56) References Cited

U.S. PATENT DOCUMENTS

| | | | |
|---|---|---|---|
| 4,890,920 A | 1/1990 | Niziolek et al. | |
| 5,206,711 A | 4/1993 | Berthold et al. | |
| 5,320,808 A * | 6/1994 | Holen et al. | 422/64 |
| 2006/0290944 A1 | 12/2006 | Arnott et al. | |
| 2010/0078581 A1 | 4/2010 | Trottier | |
| 2012/0162650 A1* | 6/2012 | Wynn et al. | 356/432 |

OTHER PUBLICATIONS

Office Action mailed Jan. 3, 2013 in U.S. Appl. No. 12/975,597, filed Dec. 22, 2010.

* cited by examiner

*Primary Examiner* — Stephen F Husar
*Assistant Examiner* — James Cranson, Jr.
(74) *Attorney, Agent, or Firm* — Edward S. Wright

(57) ABSTRACT

Self-aligning light source and detector assembly having a sensor support mounted in a predetermined, fixed position, a light source holder mounted in a predetermined, fixed position relative to the sensor support, a sensor mounted in a fixed position on the sensor support, and a lamp assembly removably mounted to the light source holder in a predetermined position defined by mating surfaces which engage each other and seat the lamp assembly in the predetermined position whenever the lamp assembly is installed in the holder.

10 Claims, 2 Drawing Sheets

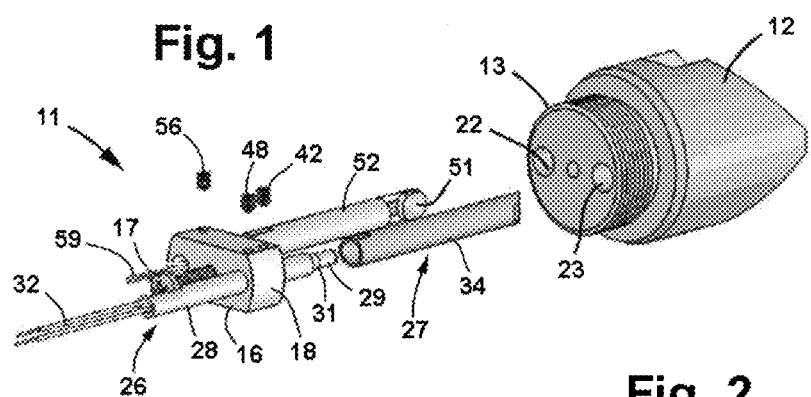
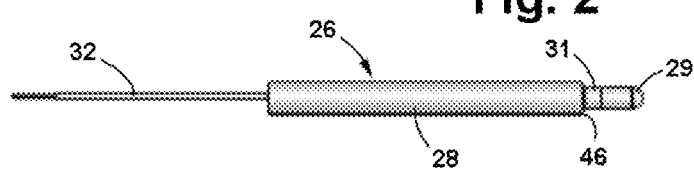
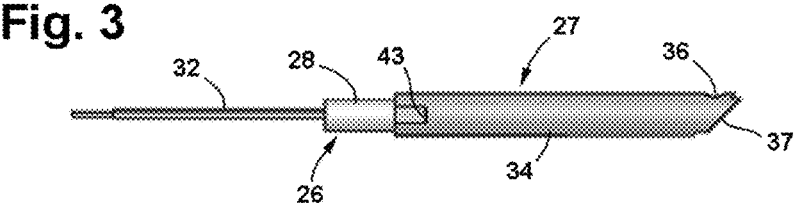
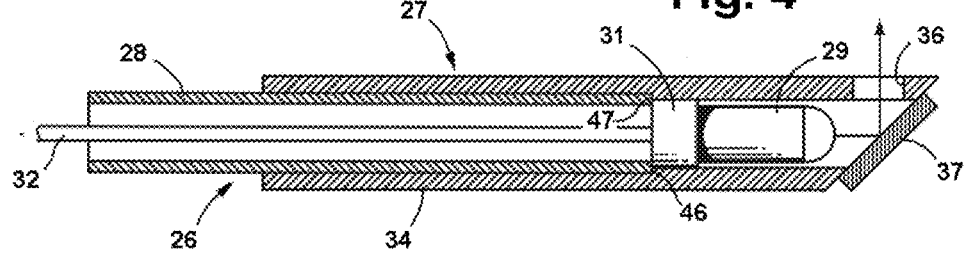
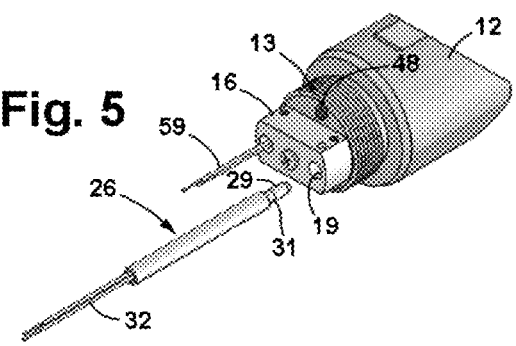

SELF-ALIGNING LIGHT SOURCE AND DETECTOR ASSEMBLY

BACKGROUND OF THE INVENTION

1. Field of Invention

This invention pertains generally to the measurement of optical absorbance and, more particularly, to a self-aligning light source and detector assembly for use in measuring optical absorbance.

2. Related Art

Instruments for measuring optical absorbance are widely used in fields such industrial, medical, and food applications. Such instruments generally include a light source and a detector, and for consistent, reliable readings, it is important that the light source and detector remain in proper alignment, particularly when the instruments are used in critical applications.

Light sources such as incandescent lamps tend to burn out and require periodic replacement, which can easily result in improper alignment and detector, particularly in smaller, more compact instruments. If the light source cannot be replaced in the field, then the instrument either has to be replaced or removed from service and sent away for repair, both of which can be expensive and disruptive.

OBJECTS AND SUMMARY OF THE INVENTION

It is, in general, an object of the invention to provide new and improved light source and detector assembly for use in measuring optical absorbance.

Another object of the invention is to provide a light source and detector assembly of the above character which the light source and detector are self-aligning.

These and other objects are achieved in accordance with the invention by providing a self-aligning light source and detector assembly having a sensor support mounted in a predetermined, fixed position, a light source holder mounted in a predetermined, fixed position relative to the sensor support, a sensor mounted in a fixed position on the sensor support, and a lamp assembly removably mounted to the light source holder in a predetermined position defined by mating surfaces which engage each other and seat the lamp assembly in the predetermined position whenever the lamp assembly is installed in the holder.

BRIEF DESCRIPTION OF THE DRAWINGS

FIG. 1 is an exploded isometric view of one embodiment of a self-aligning light source and detector assembly according to the invention.

FIG. 2 is a top plan view of the lamp assembly in the embodiment of FIG. 1.

FIG. 3 is a top plan view of the assembled light source in the embodiment of FIG. 1.

FIG. 4 is an enlarged, fragmentary sectional view of the assembled light source.

FIG. 5 is an isometric view of the embodiment of FIG. 1 with the lamp assembly removed for replacement of the lamp.

DETAILED DESCRIPTION

Figure 6:
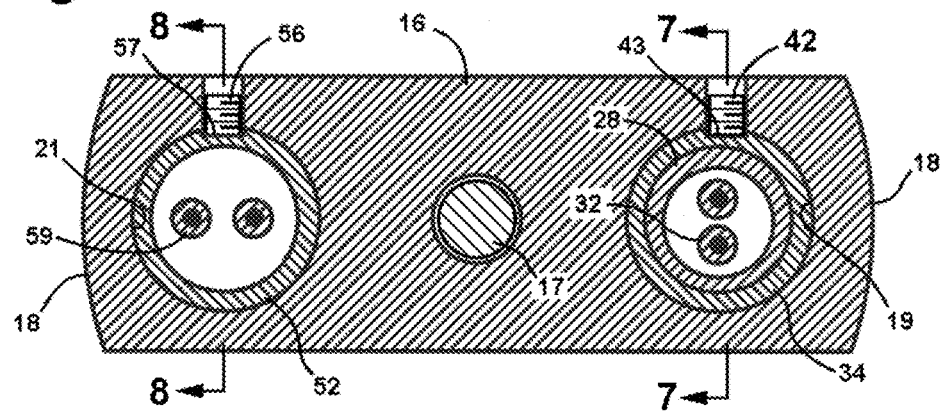
FIG. 6 is a vertical sectional view of the mounting block and associated components in the embodiment of FIG. 1.
Figure 7:
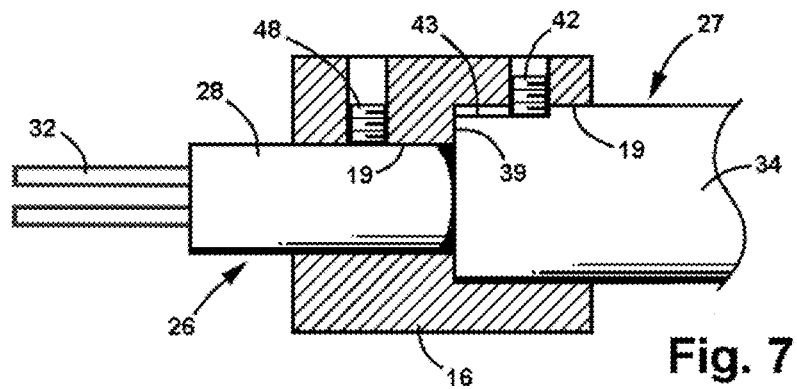
FIG. 7 is a cross-sectional view taken along line 7-7 in FIG. 6.
Figure 8:
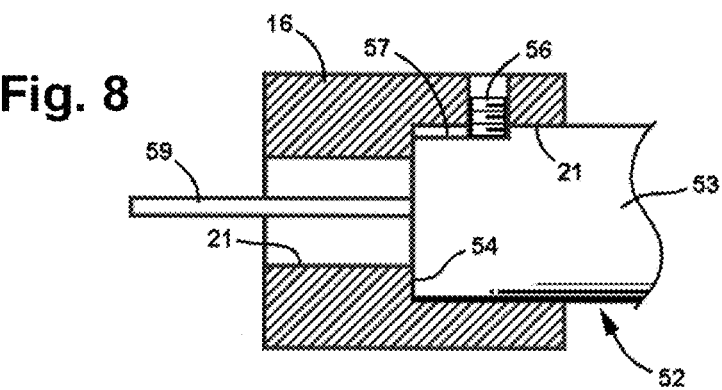
FIG. 8 is a cross-sectional view taken along line 8-8 in FIG. 6.

In FIG. 1, the light source and detector assembly 11 is illustrated in connection with a probe head 12 having an externally threaded base 13 that attaches to a generally cylindrical housing (not shown). A mounting block 16 is attached to the inner face of the base by a mounting screw 17. The block is generally rectangular, with arcuately curved end surfaces 18 of slightly smaller diameter than the inner wall of the housing. Axially extending parallel bores 19, 21 extend through the mounting block on opposite sides of the mounting screw in alignment with corresponding bores 22, 23 in the base.

The light source consists of a lamp assembly 26 which is removably mounted in a tubular holder 27. The tube holder is mounted in bore 19, passes through bore 23, and extends from the outer end of the probe head. The lamp assembly includes an elongated tubular body 28, with a lamp 29 mounted in a socket 31 at one end thereof and leads 32 extending from the socket, through the tubular body for connection to a power source in the probe housing.

The lamp holder has a tubular body 34 with an aperture 36 in the side wall thereof toward the distal or outer end of the tube and a mirror 37 mounted in the distal end portion of the tube for directing light from the lamp through the aperture toward the sensor. In the embodiment illustrated, the mirror is inclined at an angle of 45 degrees to the axis of the lamp holder, and the light from the lamp is reflected in a direction perpendicular to that axis.

The inner end of the lamp holder abuts against a radial shoulder 39 in bore 19 and is secured in place by a set screw 42 in the mounting block which is received in a key way or notch 43 in the outer wall of the lamp holder tube. Thus, when the inner end portion of the tube is inserted in the bore in abutting engagement with the shoulder and the set screw is tightened in the key way, the lamp holder is locked in a predetermined, fixed position both axially and rotatively relative to the mounting block and the probe head.

The lamp assembly is inserted coaxially into the lamp holder through the inner end of the lamp holder tube and has a radial shoulder 46 which abuts against a corresponding shoulder 47 in the tube. The lamp assembly is locked in position in the lamp holder by a set screw 48 in the mounting block which is tightened against the outer wall of the tube. Thus, the lamp assembly can be removed from the holder and then reinserted and locked a predetermined axial position. The inner end portion of the lamp assembly projects from the inner end of the holder and can be used for rotating the lamp assembly within the holder and mount for maximum optical signal before seating the set screw.

The detector assembly includes a light detector or sensing element 51 and a sensor support 52. The sensor support has an elongated tubular body 53 which is mounted in bore 21, passes through bore 22, and extends from the outer end of the probe head. The inner end of the support tube abuts against a radial shoulder 54 in bore 21 and is secured in place by a set screw 56 in the mounting block. This set screw is received in a key way or notch 57 in the outer wall of the support tube. Thus, when the inner end portion of the tube is inserted in the bore in abutting engagement with the shoulder and the set screw is tightened in the key way, the sensor support is locked in a predetermined, fixed position both axially and rotatively relative to the mounting block, the probe head, and the light source.

Light detector or sensing element 51 is mounted on the side wall of the support tube near the distal end of the tube directly opposite and facing the aperture and mirror in the lamp holder, with leads 59 from the sensing element extending through the tube for connection to circuitry in the probe housing.

To replace the lamp, the probe head is separated from the housing, set screw 48 is removed, and the lamp assembly is withdrawn from the inner end of the lamp holder, as illustrated in FIG. 5. The old lamp is removed from the socket, and a new lamp is installed in its place. The lamp assembly is then reinserted into the holder until shoulder 46 abuts against shoulder 47 and turned to maximize the signal from the detector. With the lamp assembly thus seated in its predetermined position and oriented for best signal, set screw 48 is tightened against the lamp assembly to lock it in place.

The lengths of the lamp holder and the detector assembly are such that when the inner ends of the lamp holder and sensor support tubes are seated against the shoulders in the mounting block bores and the set screws are tightened in the key ways, the sensing element is directly opposite the aperture in the lamp holder, and light reflected from the lamp by the mirror is focused on the sensing element. The alignment is self-guided and will always be the same whether the device is assembled in the factory or serviced in the field.

The alignment of the light source and sensor is not disturbed by replacement of the lamp since neither the lamp holder nor the detector assembly is moved during the process. Even if one of them did happen to move, it is easily returned its self-aligning position.

The invention has a number of important features and advantages. The light source and detector are self-aligning, and the light source lamp can be replaced in the field without disturbing that alignment.

The lamp assembly is independent of the lamp holder and projection mirror. The lamp assembly can easily be removed for lamp replacement without removal of the lamp holder and mirror which are affixed to the mounting block and probe head. The lengths of the lamp holder and the detector assembly are fixed so that when each assembly is inserted into the mounting block, its position is controlled and the two assemblies are automatically aligned to each other.

It is apparent from the foregoing that a new and improved self-aligning light source and detector assembly has been provided. While only certain presently preferred embodiments have been described in detail, as will be apparent to those familiar with the art, certain changes and modifications can be made without departing from the scope of the invention as defined by the following claims.

The invention claimed is:

1. A self-aligning light source and detector assembly, comprising: a mounting block, a sensor support mounted to the block in a first predetermined, fixed position, a light source holder mounted to the block in a second predetermined, fixed position, a sensor mounted on the sensor support in a fixed position, a lamp assembly removably mounted to the light source holder in a predetermined position defined by mating surfaces which engage each other and seat the lamp assembly in the predetermined position whenever the lamp assembly is installed in the holder, and a mirror for directing light from the lamp assembly toward the sensor when the lamp assembly is seated in the predetermined position.

2. The light source and detector assembly of claim 1 wherein the light source holder is tubular, and the lamp assembly is disposed coaxially of the tubular holder.

3. The light source and detector assembly of claim 1 wherein the lamp assembly and the light source holder have axially facing annular shoulders which abut against each other when the lamp assembly is in the predetermined position.

4. A self-aligning light source and detector assembly, comprising: a sensor support mounted in a predetermined, fixed position, a light source holder mounted in a predetermined, fixed position relative to the sensor support, a sensor mounted in a fixed position on the sensor support, and a lamp assembly removably mounted to the light source holder in a predetermined position defined by mating surfaces which engage each other and seat the lamp assembly in the predetermined position whenever the lamp assembly is installed in the holder.

5. The light source and detector assembly of claim 4 including a mirror mounted in a fixed position on the light source holder for directing light from the lamp assembly toward the sensor when the lamp assembly is seated in the predetermined position.

6. A self-aligning light source and detector assembly, comprising: a mounting block having first and second parallel bores with axially facing internal shoulders, a first support tube having a first portion in abutting engagement with the annular shoulder in the first bore and a distal end portion extending from the mounting block, a second support tube having one portion in abutting engagement with the annular shoulder in the second bore and a distal end portion extending from the mounting block in a direction parallel to the distal end portion of the first support tube, a sensor mounted in a fixed position on the first support tube facing the second support tube, a lamp assembly removably installed in a predetermined position in the second support tube with a portion of the lamp assembly in abutting engagement with an axially facing annular shoulder in the second support tube, an aperture for light in a side wall of the second support tube, and a mirror for directing light from the lamp assembly through the aperture to the sensor.

7. The light source and detector assembly of claim 6 wherein the mirror is mounted to the distal end portion of the second support tube.

8. The light source and detector assembly of claim 6 including set screws threadedly mounted in the mounting block for retaining the first and second support tubes in abutting engagement with the annular shoulders in the first and second bores and for retaining the lamp assembly in the predetermined position within the second support tube.

9. The light source and detector assembly of claim 8 wherein the first and second tubular supports have flattened areas which are engaged by the setscrews to prevent rotation of the support tubes in the mounting block.

10. The light source and detector assembly of claim 6 wherein the lamp assembly can be rotated within the second support tube for maximum optical signal from the sensor.

\* \* \* \* \*